United States Patent
Edick (10) Patent No.: US 10,518,001 B2
(45) Date of Patent: *Dec. 31, 2019

(54) BIOERODIBLE MAGNESIUM ALLOY MICROSTRUCTURES FOR ENDOPROSTHESES

(71) Applicant: Boston Scientific SciMed, Inc., Maple Grove, MN (US)

(72) Inventor: Jacob Drew Edick, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 398 days.

This patent is subject to a terminal disclaimer.

(21) Appl. No.: 15/352,111

(22) Filed: Nov. 15, 2016

(65) Prior Publication Data

US 2017/0056562 A1   Mar. 2, 2017

Related U.S. Application Data

(62) Division of application No. 14/527,317, filed on Oct. 29, 2014, now Pat. No. 9,522,220.

(Continued)

(51) Int. Cl.
*C22F 1/06* (2006.01)
*A61L 31/02* (2006.01)
(Continued)

(52) U.S. Cl.
CPC .............. *A61L 31/022* (2013.01); *A61F 2/86* (2013.01); *A61L 31/026* (2013.01);
(Continued)

(58) Field of Classification Search
CPC .. A61F 2210/0004; A61F 2/86; A61L 31/022; C22C 23/02; C22C 23/06; C22F 1/06
(Continued)

(56) References Cited

U.S. PATENT DOCUMENTS

| 4,542,539 A | 9/1985 | Rowe, Jr. et al. |
| 5,073,207 A | 12/1991 | Faure et al. |

(Continued)

FOREIGN PATENT DOCUMENTS

| EP | 1548138 | 6/2005 |
| EP | 2210625 | 7/2010 |

(Continued)

OTHER PUBLICATIONS

"Communication Pursuant to Article 94(3) EPC," for European Patent Application No. 15176192.1, dated Mar. 27, 2017 (5 pages).

(Continued)

*Primary Examiner* — Jie Yang
(74) *Attorney, Agent, or Firm* — Pauly, DeVries Smith & Deffner LLC (57) ABSTRACT

A bioerodible endoprosthesis includes a bioerodible magnesium alloy including between 50 weight percent and 92 weight percent magnesium, at least 5.5 weight percent in sum of one or more elements selected from the group consisting of Ho, Er, Lu, Tb and Tm, and at least 2.0 weight percent in sum of one or more elements selected from the group consisting of Y, Nd and Gd. The bioerodible magnesium alloy has a microstructure including equiaxed Mg-rich solid solution-phase grains having an average grain diameter of less than or equal to 15 microns and second-phase precipitates and/or ceramic nanoparticles in grain boundaries between the equiaxed Mg-rich solid solution-phase grains. The secondary-phase precipitates or ceramic nanoparticles have an average longest dimension of 2.0 micron or less. The microstructure can be produced by one or more equal-channel high-strain processes.

5 Claims, 5 Drawing Sheets

Related U.S. Application Data (60) Provisional application No. 61/896,844, filed on Oct. 29, 2013.

(51) Int. Cl.
*A61L 31/14* (2006.01)
*C22C 23/06* (2006.01)
*A61F 2/86* (2013.01)
*C22C 23/02* (2006.01)
*C22C 23/04* (2006.01)

(52) U.S. Cl.
CPC ............ *A61L 31/148* (2013.01); *C22C 23/02* (2013.01); *C22C 23/04* (2013.01); *C22C 23/06* (2013.01); *C22F 1/06* (2013.01); *A61F 2210/0004* (2013.01); *A61L 2400/12* (2013.01); *Y10T 428/12993* (2015.01)

(58) Field of Classification Search
USPC ........................................................ 148/557
See application file for complete search history.

(56) References Cited

U.S. PATENT DOCUMENTS

| | | | |
|---|---|---|---|
| 5,516,522 | A | 5/1996 | Peyman et al. |
| 5,769,884 | A | 6/1998 | Solovay |
| 5,843,172 | A | 12/1998 | Yan et al. |
| 6,240,616 | B1 | 6/2001 | Yan et al. |
| 6,287,332 | B1 | 9/2001 | Bolz et al. |
| 6,290,721 | B1 | 9/2001 | Heath et al. |
| 6,521,061 | B1 | 2/2003 | Fukunaga et al. |
| 6,686,053 | B2 | 2/2004 | Wada et al. |
| 6,716,444 | B1 | 4/2004 | Castro et al. |
| 6,723,120 | B2 | 4/2004 | Yan et al. |
| 6,770,086 | B1 | 8/2004 | Girton |
| 6,908,516 | B2 | 6/2005 | Weidemann et al. |
| 6,953,560 | B1 | 10/2005 | Castro et al. |
| 8,052,744 | B2 | 11/2011 | Girton et al. |
| 8,202,477 | B2 | 6/2012 | Papirov et al. |
| 8,449,603 | B2 | 5/2013 | Weber et al. |
| 8,840,660 | B2 | 9/2014 | Weber |
| 9,522,220 | B2 | 12/2016 | Edick |
| 9,603,728 | B2 * | 3/2017 | Stinson ................. A61L 31/022 |
| 2002/0004060 | A1 | 1/2002 | Heublein et al. |
| 2002/0197178 | A1 | 12/2002 | Yan et al. |
| 2004/0039438 | A1 | 2/2004 | Alt et al. |
| 2004/0220660 | A1 | 11/2004 | Shanley et al. |
| 2004/0267354 | A1 | 12/2004 | Ringeisen et al. |
| 2005/0119723 | A1 | 6/2005 | Peacock et al. |
| 2005/0192657 | A1 | 9/2005 | Colen et al. |
| 2005/0261760 | A1 | 11/2005 | Weber et al. |
| 2005/0283229 | A1 | 12/2005 | Dugan et al. |
| 2006/0193886 | A1 | 8/2006 | Owens et al. |
| 2006/0199876 | A1 | 9/2006 | Troczynski et al. |
| 2006/0229711 | A1 | 10/2006 | Yan et al. |
| 2006/0271168 | A1 | 11/2006 | Kleine et al. |
| 2007/0264303 | A1 | 11/2007 | Atanasoska et al. |
| 2007/0281073 | A1 | 12/2007 | Gale et al. |
| 2008/0004691 | A1 | 1/2008 | Weber et al. |
| 2008/0031765 | A1 | 2/2008 | Gerold et al. |
| 2008/0082162 | A1 | 4/2008 | Boismier et al. |
| 2008/0109072 | A1 | 5/2008 | Girton et al. |
| 2008/0195189 | A1 | 8/2008 | Asgari et al. |
| 2009/0081313 | A1 | 3/2009 | Aghion et al. |
| 2009/0088834 | A1 | 4/2009 | Wang |
| 2009/0192595 | A1 | 7/2009 | Kawamura et al. |
| 2010/0161031 | A1 | 6/2010 | Papirov et al. |
| 2010/0262222 | A1 | 10/2010 | Weber et al. |
| 2011/0172724 | A1 | 7/2011 | Hort et al. |
| 2012/0046734 | A1 | 2/2012 | Girton et al. |
| 2012/0053674 | A1 | 3/2012 | Boismier et al. |
| 2012/0059455 | A1 | 3/2012 | Weber et al. |
| 2012/0095548 | A1 | 4/2012 | Gregorich et al. |
| 2012/0215301 | A1 | 8/2012 | Papirov et al. |
| 2013/0039805 | A1 | 2/2013 | Somekawa et al. |
| 2013/0041455 | A1 | 2/2013 | Gerold |
| 2013/0090741 | A1 | 4/2013 | Guo et al. |
| 2013/0144290 | A1 | 6/2013 | Schiffl et al. |
| 2013/0331927 | A1 | 12/2013 | Zheng et al. |
| 2013/0333809 | A1 | 12/2013 | Oishi et al. |
| 2014/0200652 | A1 | 7/2014 | Bayer et al. |
| 2014/0236284 | A1 | 8/2014 | Stinson et al. |
| 2014/0277372 | A1 | 9/2014 | Ngo et al. |
| 2015/0066135 | A1 | 3/2015 | Weber et al. |
| 2015/0157767 | A1 | 6/2015 | Edick |
| 2016/0138148 | A1 | 5/2016 | Schaffer et al. |
| 2016/0263288 | A1 | 9/2016 | Edick et al. |
| 2017/0072112 | A1 | 3/2017 | Stinson |
| 2017/0106123 | A1 | 4/2017 | Weber et al. |

FOREIGN PATENT DOCUMENTS

| | | |
|---|---|---|
| EP | 2959925 | 12/2015 |
| EP | 2613817 | 3/2016 |
| EP | 3062832 | 9/2017 |
| EP | 2068964 | 11/2017 |
| JP | 2010121161 | 6/2010 |
| JP | 2016509875 | 4/2016 |
| WO | 2007082147 | 7/2007 |
| WO | 2008016150 | 2/2008 |
| WO | 2008034013 | 3/2008 |
| WO | 2008034066 | 3/2008 |
| WO | 2008036870 | 3/2008 |
| WO | 2008091835 | 7/2008 |
| WO | 2009036140 | 3/2009 |
| WO | 2009137786 | 11/2009 |
| WO | 2010003003 | 1/2010 |
| WO | 2010093244 | 8/2010 |
| WO | 2009152153 | 9/2010 |
| WO | 2010014612 | 10/2010 |
| WO | 2011011531 | 3/2011 |
| WO | 2010040084 | 6/2011 |
| WO | 2011081958 | 7/2011 |
| WO | 2011117298 | 9/2011 |
| WO | 2012003502 | 1/2012 |
| WO | 2012033637 | 3/2012 |
| WO | 2014001240 | 1/2014 |
| WO | 2014126958 | 8/2014 |
| WO | 2015066181 | 5/2015 |
| WO | 2016145368 | 9/2016 |

OTHER PUBLICATIONS

"International Preliminary Report on Patentability," for PCT Application No. PCT/US2016/022110 dated Sep. 21, 2017 (10 pages).
"Non-Final Office Action," for U.S. Appl. No. 15/392,547 dated Dec. 26, 2017 (24 pages).
"Office Action," for Japanese Patent Application No. 2015-558089 dated Oct. 17, 2017 (9 pages) with English translation.
"Response to Communication Pursuant to Article 94(3) EPC," for European Patent Application No. 15176192.1, filed with the EPO dated Jul. 17, 2017 (9 pages).
"Response to Communication Pursuant to Rules 161(1) and 162 EPC," for European Patent Application No. 16711107.9 filed with the EPO dated May 3, 2018 (10 pages).
"Response to Non-Final Office Action," for U.S. Appl. No. 15/392,547 filed with the USPTO Apr. 24, 2018 for NFOA dated Dec. 26, 2017 (8 pages).
"Second Office Action," for Chinese Patent Application No. 201480020886.4 dated Apr. 5, 2017 (6 pages).
Chakkedath, J. B. et al., "The Effect of Nd on the Tension and Compression Deformation Behavior of Extruded Mg-1Mn (wt pct) at Temperatures Between 298 K and 523 K (25 degrees C and 250 degrees C)," Metallurgical and Materials Transactions A, vol. 45A, Jul. 2014, pp. 3254-3274 (21 pages).
Cho, S. S. et al., "Structure and properties of rapidly solidified Mg—Al alloys," Journal of Materials Science 34,1999 (11 pages), 4311-4320.
"Communication Pursuant to Article 94(3) EPC," for European Patent Application No. 15176192.1, dated Nov. 25, 2015 (4 pages).

(56) References Cited

OTHER PUBLICATIONS

"Communication Pursuant to Rules 161(1) and 162 EPC," for European Patent Application No. 14706247.5, dated Oct. 30, 2015 (2 pages).
Erinc, M et al., "Applicability of Existing Magnesium Alloys as Biomedical Implant Materials," Proceedings of the Symposium held during the TMS Annual Meeting & Exhibition, San Francisco, CA, 2009, pp. 209-214.
Erinc, M. et al., "Modified AZ80 Magnesium Alloys for Biomedical Applications," Magnesium Technology, 2010, pp. 641-646 (6 pages).
"File History," for European Patent Application No. 07842447.0 downloaded from the EPO Jan. 26, 2017 (181 pages).
"File History," for European Patent Application No. 11752046.0 downloaded from the EPO dated Jan. 24, 2017 (190 pages).
"File History," for U.S. Appl. No. 11/855,019.
"File History," for U.S. Appl. No. 13/216,371.
"File History," for U.S. Appl. No. 13/284,467.
"File History," for U.S. Appl. No. 14/178,869.
"First Office Action," for Chinese Patent Application No. 201480020886.4 dated Oct. 8, 2016 (19 pages) with English Translation.
George, S. M. et al., "Molecular Layer Deposition of Organic and Hybrid Organic-Inorganic Polymers," Material Matters, 2008 (3.2), p. 34-37 (4 pages).
"International Preliminary Report on Patentability," for PCT Application No. PCT/US2014/062902, dated May 12, 2016 (9 pages).
"International Preliminary Report on Patentability," for PCT/US2007/078417 dated Mar. 17, 2009 (7 pages).
"International Preliminary Report on Patentability," for PCT/US2009/046750 dated Dec. 23, 2010 (7 pages).
"International Preliminary Report on Patentability," for PCT/US2009/059424 dated May 5, 2011 (7 pages).
"International Preliminary Report on Patentability," for PCT/US2011/048954 dated Mar. 12, 2013 (7 pages).
"International Preliminary Report on Patentability," for PCT/US2014/015932, dated Aug. 18, 2015 (9 pages).
"International Search Report & Written Opinion," for PCT/US2007/078417, dated Jan. 22, 2009 (14 pages).
"International Search Report & Written Opinion," for PCT/US2014/015932, dated May 22, 2014 (11 pages).
"International Search Report & Written Opinion," for PCT/US2014/062902, dated Feb. 18, 2015 (12 pages).
"International Search Report and Written Opinion," for PCT Application No. PCT/US2016/022110, dated May 24, 2016 (12 pages).
"International Search Report and Written Opinion," for PCT/US2011/048954 dated Oct. 19, 2011 (10 pages).
"International Search Report," for PCT/US2009/046750 dated Jul. 20, 2010 (4 pages).
"International Search Report," for PCT/US2009059424 dated Apr. 21, 2011 (4 pages).
Joshi, S. et al., "High Shear Deformation to Produce High Strenght and Energy Absorption in Mg Alloys," Editor Martyn Alderman et al., Magnesium Technology 2014, TMS (The Minerals, Metals, and Materials Society), 2014, Wiley Publishers, pp. 83-88.
Khan, Mohammad N. "Solidification study of commercial magnesium alloys," Master's Thesis, Concordia University, Montreal, Quebec, Canada, Oct. 2009 (105 pages).
Kim, et al., "Continuous Casting of Magnesium Alloy Billet Using Electromagnetic Techniques," Materials Science Forum vols. 654-656, Nie and Morton, Jun. 2010 (3 pages) 787-790.
Milner, F. et al., "Microstructural Evolution and Its Relationship to the Mechanical Properties of Mg AZ31B Friction Stir Back Extruded Tubes," Editor Martyn Alderman et al., Magnesium Technology 2014, TMS (The Minerals, Metals, and Materials Society), 2014, Wiley Publishers, pp. 263-268.
"Notice of Allowance," for U.S. Appl. No. 14/527,317 dated Sep. 23, 2016 (19 pages).
Park, Won-Wook et al., "Microstructural change and precipitation hardening in melt-spun Mg—X—Ca alloys," Science and Technology of Advanced Materials (2001), 2:1 73-78 (7 pages).

"Response to Communication Pursuant to Article 94(3) EPC," for European Patent Application No. 15176192.1, filed with the EPO dated Mar. 21, 2016 (58 pages).
"Response to Communication Pursuant to R161(1) and 162 EPC," for European Patent Application No. 14706247.5, dated Oct. 30, 2015 and filed with the EPO dated Dec. 17, 2015 (17 pages).
"Response to Communication Pursuant to Rules 161(1) and 162 EPC," for European Patent Application No. 141796368.0 filed with the EPO dated Jan. 2, 2017 (12 pages).
Seman, Michael et al., "Self-Limiting Growth of Tantalum Oxide Thin Films by Pulsed Plasma-Enhanced Chemical Vapor Deposition," Applied Physics Letters, 2007, 90: 131504 (3 pages).
Xu, Guang-Liang et al., "Effect of Equal Channel Angular Extrusion on the Microstructure and Mechanical Properties of AZ31 Magnesium Alloy," Material Engineering, vol. 2, Feb. 28, 2011, pp. 69-72, with English Translation (8 pages).
Zhou, Y. et al., "Microstructure Evolution and Mechanical Behavior of Mg-10Gd-3Y-0.4Zr Alloy Processed by ECAP at High Temperature," Editor Martyn Alderman et al., Magnesium Technology 2014, TMS (The Minerals, Metals, and Materials Society), 2014, Wiley Publishers, pp. 511-516.
Final Office Action for U.S. Appl. No. 15/392,547 dated Aug. 16, 2018 (19 pages).
First Office Action for Chinese Patent Application No. 201480071292.6 dated Jun. 6, 2018 (9 pages).
Non-Final Office Action for U.S. Appl. No. 15/068,132 dated Jun. 29, 2018 (34 pages).
Office Action for Japanese Patent Application No. 2016-526876 dated Jul. 3, 2018 (13 pages) with English translation.
Response to Non-Final Rejection dated Jun. 29, 2018, for U.S. Appl. No. 15/068,132, submitted via EFS-Web on Aug. 22, 2018, 12 pages.
Non Final Office Action for U.S. Appl. No. 15/358,636 dated Apr. 11, 2019 (36 pages).
Non Final Office Action for U.S. Appl. No. 15/392,547 dated Mar. 22, 2019 (20 pages).
Response to Final Rejection dated Nov. 29, 2018, for U.S. Appl. No. 15/068,132, submitted via EFS-Web on Mar. 25, 2019, 17 pages.
Second Office Action for Chinese Patent Application No. 201480071292.6 dated Feb. 19, 2019 (12 pages) with English Translation.
Communication Pursuant to Article 94(3) EPC, for European Patent Application No. 16711107.9 dated Dec. 21, 2018 (7 pages).
Final Office Action for U.S. Appl. No. 15/068,132 dated Nov. 29, 2018 (19 pages).
Office Action for Japanese Patent Application No. 2016-526876 dated Jan. 29, 2019 (7 pages) with English Translation.
Response to Final Rejection dated Aug. 16, 2018, for U.S. Appl. No. 15/392,547, submitted via EFS-Web on Jan. 15, 2019, 12 pages.
Friedrich, Horst E. et al., "Magnesium Technology—Metallurgy, Design Data, Applications," Springer, 2006 (22 pages).
Hermawan, Hendra "Biodegradable Metals—From Concept to Applications," Springer, 2012 (8 pages).
Jin, Li et al., "Mechanical properties and microstructure of AZ31 Mg Alloy processed by two-step equal channel angular extrusion," Materials Letters, vol. 59, 2005 (4 pages).
Lee, Y. C. et al., "The Role of Solute in Grain Refinement of Magnesium," Metallurgical and Materials Transactions A, vol. 31A, Nov. 2000 (12 pages).
Non-Final Office Action for U.S. Appl. No. 15/068,132 dated May 3, 2019 (27 pages).
Notice of Opposition for European Patent Application No. 14706247.5 on behalf of Biotronik AG, dated May 14, 2019 and May 17, 2019 (26 pages).
Rad, Hamid R. et al., "Characterization and corrosion behavior of biodegradable Mg—Ca and Mg—Ca—Zn implant alloys," Applied Mechanics and materials, vol. 121, Oct. 24, 2011 (6 pages).
Serruys, Patrick W. et al., "Handbook of Coronary Stents," Martin Dunitz Ltd., 2000 (11 pages).
Wu, Qiong et al., "The microstructure and properties of cyclic extrusion compression treated Mg—Zn—Y—Nd Alloy for vascular (56) References Cited

OTHER PUBLICATIONS stent application," Journal of the Mechanical Behavior of Biomedical Materials, vol. 8, Apr. 2012 (8 pages).

* cited by examiner

BIOERODIBLE MAGNESIUM ALLOY MICROSTRUCTURES FOR ENDOPROSTHESES

This application is a divisional of U.S. application Ser. No. 14/527,317, filed Oct. 29, 2014, which claims the benefit of U.S. Provisional Application No. 61/896,844, filed Oct. 29, 2013, the contents of which are herein incorporated by reference in their entireties.

TECHNICAL FIELD

This disclosure relates to microstructures for bioerodible magnesium alloys used in endoprostheses and methods of producing those microstructures.

BACKGROUND

Endoprostheses can be used to replace a missing biological structure, support a damaged biological structure, and/or enhance an existing biological structure. Frequently, only a temporary presence of the endoprosthesis in the body is necessary to fulfill the medical purpose. Surgical intervention to remove endoprostheses, however, can cause complications and may not even be possible. One approach for avoiding a permanent presence of all or part of an endoprosthesis is to form all or part of the endoprosthesis out of bioerodible material. The term "bioerodible" as used herein is understood as the sum of microbial procedures or processes solely caused by the presence of endoprosthesis within a body, which results in a gradual erosion of the structure formed of the bioerodible material.

At a specific time, the endoprosthesis, or at least the part of the endoprosthesis that includes the bioerodible material, loses its mechanical integrity. The erosion products are mainly absorbed by the body, although small residues can remain under certain conditions. A variety of different bioerodible polymers (both natural and synthetic) and bioerodible metals (particularly magnesium and iron) have been developed and are under consideration as candidate materials for particular types of endoprostheses. Many of these bioerodible materials, however, have significant drawbacks. These drawbacks include the erosion products, both in type and in rate of release, as well as the mechanical properties of the material.

SUMMARY

A bioerodible endoprosthesis provided herein includes a bioerodible magnesium alloy including between 50 weight percent and 92 weight percent magnesium, a total content of at least 5.5 weight percent of Ho, Er, Lu, Tb, and Tm in sum, and a total content of at least 2 weight percent of Y, Nd, and Gd in sum. The bioerodible magnesium alloy is formed such that it has a microstructure defined by equiaxed Mg-rich solid solution-phase grains (i.e., alpha-phase grains) having an average grain diameter of less than or equal to 15 microns. In some cases, secondary phase precipitates can be located in grain boundaries between the equiaxed Mg-rich solid solution-phase grains. In some cases, the ceramic nanoparticles can be located in grain boundaries between the equiaxed Mg-rich solid solution-phase grains. In some cases, the secondary phase precipitates and/or ceramic nanoparticles can have an average longest dimension of 500 nanometers or less. Bioerodible magnesium alloys having the microstructures provided herein can have improved mechanical properties suitable for endoprostheses, such as stents.

A method of processing a bioerodible magnesium alloy for endoprostheses provided herein can include the steps of forming an ingot or billet of molten magnesium alloy and performing at least one high-strain process on the ingot or billet to form the grain morphology provided herein. In some cases, the processing can include holding the ingot or billet at a temperature above the solvus temperature (e.g., between 400° C. and 450° C.) for at least 2 hours to homogenize the ingot or billet prior to performing the at least one high-strain process. The at least one high-strain process can be an equal-channel high-strain process and can be conducted at a temperature of less than the solvus temperature (e.g., a temperature below 400° C.). In some cases, multiple equal-channel high-strain processes are conducted using subsequently lower temperatures.

A bioerodible magnesium alloy formulation can include magnesium and a plurality of rare earth metals. In some cases, the rare earth metals can include scandium (Sc), yttrium (Y), lanthanum (La), neodymium (Nd), gadolinium (Gd), terbium (Tb), dysprosium (Dy), holmium (Ho), erbium (Er), thulium (Tm), and/or lutetium (Lu). In some cases, the bioerodible magnesium alloy can include zirconium (Zr), calcium (Ca), zinc (Zn), and/or indium (In). In some cases, a bioerodible magnesium alloy provided herein can include at least 5.5 weight percent in sum of one or more elements selected from the group consisting of selected from the group consisting of Ho, Er, Lu, Tb and Tm. In some cases, a bioerodible magnesium alloy provided herein can include at least 2.0 weight percent in sum of one or more elements selected from the group consisting of selected from the group consisting of Y, Nd and Gd. In some cases, a bioerodible magnesium alloy provided herein can include aluminum, zinc, calcium, manganese, tin, neodymium, yttrium, cerium, lanthanum, gadolinium, or a combination thereof. In some cases, a bioerodible magnesium alloy provided here in can consist of:

Y: 0-10.0 weight percent;
Nd: 0-4.5 weight percent;
Gd: 0-9.0 weight percent;
Dy: 0-8.0 weight percent;
Ho: 0-19.0 weight percent;
Er: 0-23.0 weight percent;
Lu: 0-25.0 weight percent;
Tm: 0-21.0 weight percent;
Tb: 0-21.0 weight percent;
Zr: 0.1-1.5 weight percent;
Ca: 0-2.0 weight percent;
Zn: 0-1.5 weight percent;
In: 0-12.0 weight percent;
Sc: 0-15.0 weight percent;
incidental impurities up to a total of 0.3 weight percent; and
the balance being magnesium and under the condition that a total content of Ho, Er, Lu, Tb and Tm is more than 5.5 weight percent; a total content of Y, Nd and Gd is more than 2.0 weight percent; and a total content of all alloy compounds except magnesium is more than 8.5 weight percent. In some cases, a bioerodible magnesium alloy provided herein includes between 70 weigh percent and 91.5 weight percent magnesium.

In some cases, ceramic nanoparticles can be added to the alloy. Ceramic nanoparticles provided herein can include any suitable ceramic material. In some cases, the ceramic nanoparticles can be insoluble in the bioerodible magnesium alloy. In some cases, ceramic nanoparticles can include one or more of the following ceramic materials: TiC, $TiO_2 Si_3 N_4$, AlN, $Al_2O_3$, $CeO_2$, Boron Nitride, $B_4C$, and $Y_2O_3$.

Endoprostheses provided herein can have any suitable structure. In some cases, an endoprostheis provided herein is a stent. For example, a stent provided herein can include plurality of struts arranged to form a generally tubular structure that can be expanded or retracted between a plurality of different diameters. In some cases, an endoprosthesis provided herein can consist of a magnesium alloy or magnesium alloy composite provided herein. In some cases, an endorposthesis provided herein can include one or more additional materials. For example, in some cases an endoprosthesis provided herein can include a coating. In some cases, a coating provided on an endoprosthesis provided herein has a thickness of between 5 nm and 20 nm. In some cases, a coating provided on an endoprosthesis provided herein includes titanium oxide, aluminum oxide, or a combination thereof. In some cases, a coating provided on an endoprosthesis provided herein includes a therapeutic agent.

One advantage of an endoprosthesis including a bioerodible magnesium alloy having a microstructure or composite structure provided herein is that the resulting endoprosthesis' mechanical properties and degradation rate can be tailored to maintain desired mechanical properties over a desired period of time and an optimal bioerosion rate. A bioerodible magnesium alloy having a microstructure provided herein can have improved ductility as compared to similar alloys having different microstructures. In some cases, ceramic nanoparticles provided in a composite provided herein can simplify a grain refinement procedure by pinching grain boundaries and inhibiting grain growth during one or more high-strain processes.

The details of one or more embodiments are set forth in the accompanying drawings and the description below. Other features, objects, and advantages will be apparent from the description and drawings, and from the claims.

DESCRIPTION OF DRAWINGS

FIGS. 4A-4D show SBF Immersion results for stents.

DETAILED DESCRIPTION

Figure 1:
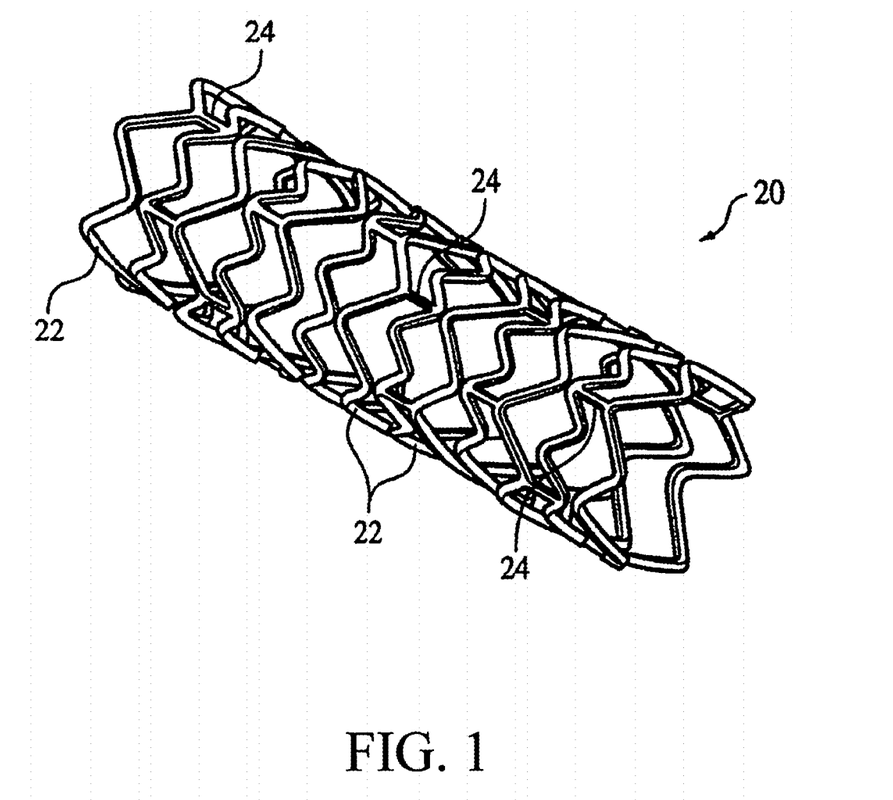
FIG. 1 is a perspective view of a representative stent.

A stent 20, shown in FIG. 1, is an example of an endoprosthesis. Stent 20 includes a pattern of interconnected struts forming a structure that contacts a body lumen wall to maintain the patency of the body lumen. For example, stent 20 can have the form of a tubular member defined by a plurality of bands 22 and a plurality of connectors 24 that extend between and connect adjacent bands. During use, bands 22 can be expanded from an initial, small diameter to a larger diameter to contact stent 20 against a wall of a vessel, thereby maintaining the patency of the vessel. Connectors 24 can provide stent 20 with flexibility and conformability that allow the stent to adapt to the contours of the vessel. Other examples of endoprostheses include covered stents and stent-grafts.

At least one strut of stent 20 can be adapted to erode under physiological conditions. In some cases, stent 20 is fully bioerodible. Stent 20 can include a composite of a matrix including a bioerodible magnesium alloy including a plurality of rare earth metals. In some cases, the rare earth metals can include scandium (Sc), yttrium (Y), lanthanum (La), neodymium (Nd), gadolinium (Gd), terbium (Tb), dysprosium (Dy), holmium (Ho), erbium (Er), thulium (Tm), and/or lutetium (Lu). In some cases, the bioerodible magnesium alloy can include zirconium (Zr), calcium (Ca), zinc (Zn), and/or indium (In). In some cases, a bioerodible magnesium alloy provided herein can include at least 5.5 weight percent in sum of one or more elements selected from the group consisting of selected from the group consisting of Ho, Er, Lu, Tb and Tm. In some cases, a bioerodible magnesium alloy provided herein can include at least 2.0 weight percent in sum of one or more elements selected from the group consisting of selected from the group consisting of Y, Nd and Gd. In some cases, a bioerodible magnesium alloy provided herein can include at least 3.0 weight percent in sum of one or more elements selected from the group consisting of selected from the group consisting of Y, Nd and Gd.

A bioerodible magnesium alloy formulation provided herein can have a Y content of between 0-10.0 weight percent. In some cases, a bioerodible magnesium alloy formulation provided herein can have a Y content of between 1.0-6.0 weight percent. In some cases, a bioerodible magnesium alloy formulation provided herein can have a Y content of between 3.0-4.0 weight percent.

A bioerodible magnesium alloy formulation provided herein can have a Nd content of between 0-4.5 weight percent. In some cases, a bioerodible magnesium alloy formulation provided herein can have a Nd content of between 0.05-2.5 weight percent.

A bioerodible magnesium alloy formulation provided herein can have a Gd content of between 0-9 weight percent. In some cases, a bioerodible magnesium alloy formulation provided herein can have a Gd content of between 0-4.0 weight percent.

A bioerodible magnesium alloy formulation provided herein can have a Dy content of between 0-8.0 weight percent. In some cases, a bioerodible magnesium alloy formulation provided herein can have a Dy content of between 0-6.0 weight percent. In some cases, a bioerodible magnesium alloy formulation provided herein can have a Dy content of between 0-4.0 weight percent.

In some cases, a bioerodible magnesium alloy formulation provided herein can have a Ho content of between 0-19.0 weight percent. In some cases, a bioerodible magnesium alloy formulation provided herein can have a Ho content of between 4.0-15.0 weight percent. In some cases, a bioerodible magnesium alloy formulation provided herein can have a Ho content of between 6.0-14.0 weight percent.

A bioerodible magnesium alloy formulation provided herein can have a Er content of between 0-23.0 weight percent. In some cases, a bioerodible magnesium alloy formulation provided herein can have a Er content of between 4.0-15.0 weight percent. In some cases, a bioerodible magnesium alloy formulation provided herein can have a Er content of between 6.0-14.0 weight percent.

A bioerodible magnesium alloy formulation provided herein can have a Lu content of between 0-25.0 weight percent. In some cases, a bioerodible magnesium alloy formulation provided herein can have a Lu content of between 4.0-15.0 weight percent. In some cases, a bioerodible magnesium alloy formulation provided herein can have a Lu content of between 6.0-14.0 weight percent.

A bioerodible magnesium alloy formulation provided herein can have a Tm and/or Tb content of between 0-21.0 weight percent. In some cases, a bioerodible magnesium alloy formulation provided herein can have a Tm and/or Tb content of between 4.0-15.0 weight percent. In some cases, a bioerodible magnesium alloy formulation provided herein can have a Tm and/or Tb content of between 6.0-12.0 weight percent.

A bioerodible magnesium alloy formulation provided herein can total content of Ho, Er, Lu, Tb and Tm of more than 5.5 weight percent in sum. In some cases, a bioerodible magnesium alloy formulation provided herein can total content of Ho, Er, Lu, Tb and Tm of between 6.5-25.0 weight percent. In some cases, a bioerodible magnesium alloy formulation provided herein can total content of Ho, Er, Lu, Tb and Tm of between 7.0-15.0 weight percent.

A bioerodible magnesium alloy formulation provided herein can have a Sc content of between 0-15 weight percent.

The solubility of rare earth metals in magnesium varies considerably, and the addition of the amounts of rare earth metals provided herein can result secondary phase precipitates. In some cases, a volume of coarse secondary phase precipitates present would be primarily related to the Nd content, due to its low solid solubility in magnesium. Processing techniques provided herein, however, can create a microstructure where the coarse secondary phase precipitates have an average longest dimension of 2.0 microns or less and be primarily centered in the grain boundaries of magnesium-rich solid solution alpha-phase grains. Processing techniques provided herein, however, can create a microstructure where the coarse secondary phase precipitates have an average longest dimension of 1.0 microns or less and be primarily centered in the grain boundaries of magnesium-rich solid solution alpha-phase grains. Processing techniques provided herein, however, can create a microstructure where the coarse secondary phase precipitates have an average longest dimension of 500 nanometers or less and be primarily centered in the grain boundaries of magnesium-rich solid solution alpha-phase grains. In some cases, processing techniques provided herein can create a microstructure where at least 80% of coarse secondary phase precipitates have a longest dimension of 2.0 microns or less and be primarily centered in the grain boundaries of magnesium-rich solid solution alpha-phase grains. In some cases, processing techniques provided herein can create a microstructure where at least 90% of coarse secondary phase precipitates have a longest dimension of 2.0 microns or less and be primarily centered in the grain boundaries of magnesium-rich solid solution alpha-phase grains. In some cases, processing techniques provided herein can create a microstructure where at least 95% of coarse secondary phase precipitates have a longest dimension of 2.0 microns or less and be primarily centered in the grain boundaries of magnesium-rich solid solution alpha-phase grains. In some cases, processing techniques provided herein can create a microstructure where at least 80% of coarse secondary phase precipitates have a longest dimension of 1.0 microns or less and be primarily centered in the grain boundaries of magnesium-rich solid solution alpha-phase grains. In some cases, processing techniques provided herein can create a microstructure where at least 90% of coarse secondary phase precipitates have a longest dimension of 1.0 microns or less and be primarily centered in the grain boundaries of magnesium-rich solid solution alpha-phase grains. In some cases, processing techniques provided herein can create a microstructure where at least 95% of coarse secondary phase precipitates have a longest dimension of 1.0 microns or less and be primarily centered in the grain boundaries of magnesium-rich solid solution alpha-phase grains. In some cases, processing techniques provided herein can create a microstructure where at least 80% of coarse secondary phase precipitates have a longest dimension of 500 nanometers or less and be primarily centered in the grain boundaries of magnesium-rich solid solution alpha-phase grains. In some cases, processing techniques provided herein can create a microstructure where at least 90% of coarse secondary phase precipitates have a longest dimension of 500 nanometers or less and be primarily centered in the grain boundaries of magnesium-rich solid solution alpha-phase grains. In some cases, processing techniques provided herein can create a microstructure where at least 95% of coarse secondary phase precipitates have a longest dimension of 500 nanometers or less and be primarily centered in the grain boundaries of magnesium-rich solid solution alpha-phase grains. Processing techniques provided herein can create relatively equiaxed magnesium-rich solid solution alpha-phase grains having an average grain diameter of less than or equal to 15 microns (longest dimension in a metallography cross-section plane). Processing techniques provided herein can create relatively equiaxed magnesium-rich solid solution alpha-phase grains having an average grain diameter of less than or equal to 10 microns (longest dimension in a metallography cross-section plane). Processing techniques provided herein can create relatively equiaxed magnesium-rich solid solution alpha-phase grains having an average grain diameter of less than or equal to 5 microns (longest dimension in a metallography cross-section plane).

A bioerodible magnesium alloy formulation provided herein can have a Zr content of between 0.1-1.5 weight percent. In some cases, a bioerodible magnesium alloy formulation provided herein can have a Zr content of between 0.2-0.6 weight percent. In some cases, a bioerodible magnesium alloy formulation provided herein can have a Zr content of between 0.2-0.4 weight percent.

A bioerodible magnesium alloy formulation provided herein can have a Ca content of between 0-2.0 weight percent. In some cases, a bioerodible magnesium alloy formulation provided herein can have a Ca content of between 0-1.0 weight percent. In some cases, a bioerodible magnesium alloy formulation provided herein can have a Ca content of between 0.1-0.8 weight percent.

A bioerodible magnesium alloy formulation provided herein can have a Zn content of between 0-1.5 weight percent. In some cases, a bioerodible magnesium alloy formulation provided herein can have a Zn content of between 0-0.5 weight percent. In some cases, a bioerodible magnesium alloy formulation provided herein can have a Zn content of between 0.1-0.3 weight percent.

A bioerodible magnesium alloy formulation provided herein can have a In content of between 0-12.0 weight percent. In some cases, a bioerodible magnesium alloy formulation provided herein can have a In content of between 0-2.5 weight percent. In some cases, a bioerodible magnesium alloy formulation provided herein can have a In content of between 0.0-0.8 weight percent.

A bioerodible magnesium alloy formulation provided herein can, in some cases, have a total content of In, Zr, Ca and Zn in the Mg alloy in the range of 0.2-2.0 weight percent. In some cases, a bioerodible magnesium alloy formulation provided herein can have a total content of In, Zr, Ca and Zn in the Mg alloy in the range of 0.2-0.8 weight percent.

A bioerodible magnesium alloy formulation provided herein can, in some cases, have a total content of impurities of less than 0.3 weight percent. In some cases, a bioerodible magnesium alloy formulation provided herein can have a total content of impurities of less than 0.2 weight percent. In some cases, a bioerodible magnesium alloy formulation provided herein can have a maximum of 0.05 weight percent of each of Fe, Si, Cu, Mn, and Ag. In some cases, a bioerodible magnesium alloy formulation provided herein can have a maximum of 0.006 weight percent of Ni. In some cases, a bioerodible magnesium alloy formulation provided herein can have a maximum of 0.15 weight percent of each of La, Ce, Pr, Sm, Eu and Yb. In some cases, a bioerodible magnesium alloy formulation provided herein can have a maximum of 0.1 weight percent of each of La, Ce, Pr, Sm, Eu and Yb.

The secondary-phase precipitates can have an average longest dimension of 500 nanometers or less can be formed in bioerodible magnesium alloys provided herein using processes provided herein. Secondary-phase precipitates can be predominantly located in grain boundaries rather than within grains (e.g., >50% of the combined area of second-phase precipitates are on grain boundaries in a given prepared metallography cross-section plane examined at 100-300× magnification). For example, a majority of the second-phase precipitates (i.e., the secondary-phase) can located are located in grain boundaries rather than within the Mg-rich solid solution-phase grains. Magnesium alloys having the microstructures provided herein can have improved mechanical properties suitable for endoprostheses, such as stents. In some cases, ceramic nanoparticles can be added to the alloy during the process and can also have an average longest dimension of 500 nanometers or less and be predominantly located in grain boundaries rather than within grains.

Although magnesium and magnesium alloys have been explored as candidate materials for bioerodible endoprostheses in the past, the mechanical properties of magnesium and magnesium alloys have presented certain difficulties that make the use of a bioerodible magnesium metal or alloy in certain endoprostheses, such as stents, impractical. In particular, magnesium alloys can have a limited ductility due to a lack of available slip planes in the Hexagonal Close Packed (HCP) crystal lattice. Slip planes can accommodate plastic deformation. Limited ductility can complicate certain uses that rely upon plastic deformation. For example, limited ductility can make stent crimping and stent expansion more complex due to an increased probability of stent fractures during these plastic deformations. Moreover, magnesium alloys typically have a lower tensile strength than iron alloys (such as stainless steel alloys). Bioerodible magnesium alloys having a microstructure provided herein, however, can have improved ductility and tensile strength.

Certain magnesium alloys were tested in order to identify magnesium alloys having suitable bioerosion rates and ductility. For example, L1c and WE43 (described in Table I below) were prototyped and tested as stents, but found to have a bioerosion rate that was too fast when subjected to in-vivo and in-vitro testing. It is possible, however, that a L1c and/or WE43 alloy having a microstructure provided herein would have a suitable bioerodison rate for an endoprosthesis.

TABLE I

| Alloy Ex. | Zn | Zr | Mn | Y | Ca | Ag | Fe | Other Elements | Mg |
|---|---|---|---|---|---|---|---|---|---|
| L1c | 2.87 | ≤0.02 | 0.15 | — | 0.22 | 0.10 | 0.0036 | — | Balance |
| WE43 | 0.20 | 0.36 | 0.13 | 4.16 | — | — | — | 3.80 | 91.35 |

Certain modifications of the AZ80 alloy (see Table II below) have also been developed in an attempt to find a magnesium alloy having superior corrosion resistance to that of L1c, but also having sufficient ductility. Although initial mechanical testing of these AZ80 modified alloys showed an improvement in the mechanical and corrosion properties as compared to L1c, AZ80 modified alloy stents cracked and fractured at a nominal expanded diameter. A stent made from AZNd alloy using a process described herein, however, demonstrated good mechanical properties, as discussed below.

TABLE II

| Alloy Example | Al | Zn | Mn | Y | Nd | La | Mg |
|---|---|---|---|---|---|---|---|
| AZ80 | 7.5 | 0.5 | 0.2 | — | — | — | Balance |
| AZNd | 7.3 | 0.6 | 0.1 | — | 0.7 | — | Balance |
| AZY | 7.4 | 0.6 | 0.1 | 0.5 | — | — | Balance |
| AZNdY | 7.0 | 0.6 | 0.2 | 0.5 | 0.6 | — | Balance |
| AZM | 7.3 | 0.6 | 0.4 | — | — | — | Balance |
| AZL | 7.0 | 0.5 | 0.2 | — | — | 1.2 | Balance |
| AE82 | 8.0 | 0.5 | 0.2 | 0.5 | 1.0 | — | Balance |

An analysis of the stents identified the presence of large extrinsic intermetallic particles, e.g., oxide inclusions and coarse Mg solid solution grain sizes, which are deleterious to ductility. Low material ductility can result in stent cracking, especially in balloon-expandable stents that are crimped onto a balloon catheter, guided through a long tortuous path, and expanded to fill the diameter of the artery.

Microstructures and processes provided herein can eliminate this root cause of low material ductility and stent cracking by having lower extrinsic inclusion content (or at least much smaller inclusions), and stent material with refined Mg solid solution grain size to randomize grain texture, produce additional slip systems through grain size refinement and raise the activation energy needed to initiate a crack due to the presence of a tortuous grain boundary network. Microstructures and processes provided herein can be tailored to manifest sufficient ductility in a balloon-expandable stent design such that the Mg alloy stent would allow the stent to be crimped onto a balloon catheter, wiggled through a long tortuous path, and expanded to fill the diameter of the artery without fracturing.

A microstructure of material can be at least partially dependent on the processing techniques and parameters. The grains (i.e., crystals) of a magnesium alloy can align themselves with their basal planes parallel to the direction of the processing material flow, which can result in different mechanical properties in the direction of flow as compared to the direction perpendicular to the direction of flow. In the case of extruding stent tubing including the alloys of Table II, the resulting tube may have a strong preferred crystal orientation, aligning the basal planes in the extrusion direction, which produces increased ductility in the extrusion direction of the tubing, but less ductility in a direction perpendicular to the extrusion direction. The expansion of a stent, however, relies upon the material having suitable ductility in all directions. A strong grain texture with an unfavorable loading along the c-crystal axis components of the grains causes twinning and void nucleation under lower strains. The twinning with void nucleation can be the initiation of an eventual material failure. Stent tube extrusion may also produce a randomized crystal structure with no preferred orientation, which produces more isotropic mechanical properties, but still suffers from the ductility issues discussed above.

Microstructures provided herein can provide superior ductility and other mechanical properties in multiple directions. Grain boundaries are decorated with precipitates and/or ceramic nanoparticles. Microstructures provided herein can be characterized in a number of ways. In some cases, the microstructures provided herein, when viewed at a 500× using x-ray diffraction, have no more than 3% by area filled with intermetallic ("IM") particles. In some case, the microstructures provided herein have no more than 2% by area filled with IM particles. In some cases, a maximum IM particle dimension will be 30 microns or less. In some cases, a maximum IM particle dimension will be 20 microns or less, 10 microns or less, 5 microns or less, or 1 micron or less.

In some cases, the grain boundaries can be decorated with ceramic nanoparticles. Ceramic nanoparticles can pinch grain boundaries and/or impede grain growth during processing of the material, which can result in a fine grain microstructure of the magnesium alloy. The fine grain microstructure of the magnesium alloy can increase strength and ductility of the material. In some case, the microstructures provided herein have at least 0.5% by area filled with ceramic particles. In some case, the microstructures provided herein have at least 1.0% by area filled with ceramic particles. In some case, the microstructures provided herein have between 0.5% and 5% by area filled with ceramic particles. In some case, the microstructures provided herein have between 1.0% and 3% by area filled with ceramic particles. In some case, the microstructures provided herein have about 1.5% by area filled with ceramic particles.

Ceramic nanoparticles provided in a composite provided herein can have any appropriate dimensions. In some cases, ceramic nanoparticles used in a composite provided herein have an average largest diameter of between 0.5 nanometers and 500 nanometers, between 1.0 nanometer and 200 nanometers, between 5 nanometers and 100 nanometers, between 10 nanometers and 100 nanometers, between 25 nanometers and 75 nanometers, or between 40 nanometers and 60 nanometers. In some cases, a maximum ceramic nanoparticle dimension will be 5 micron or less. In some cases, a maximum ceramic nanoparticle dimension will be 1 micron or less, 500 nanometers or less, 5 microns or less, or 200 nanometers or less.

Ceramic nanoparticles provided in a composite provided herein can include any suitable ceramic material. In some cases, ceramic nanoparticles provided herein are insoluble in a magnesium alloy used in a composite provided herein. In some cases, ceramic nanoparticles can include one or more of the following ceramic materials: TiC, $TiO_2Si_3N_4$, AlN, $Al_2O_3$, $CeO_2$, Boron Nitride, $B_4C$, and $Y_2O_3$. In some cases, ceramic nanoparticles used in a composite provided herein include a radiopaque ceramic material. In some cases, ceramic nanoparticles used in a composite provided herein can have an electro-motive force within 50% of the electro-motive force of magnesium. In some cases, ceramic nanoparticles used in a composite provided herein can have an electro-motive force within 25% of the electro-motive force of magnesium. In some cases, ceramic nanoparticles used in a composite provided herein can have an electro-motive force within 10% of the electro-motive force of magnesium. In some cases, ceramic nanoparticles used in a composite provided herein can have an electro-motive force within 5% of the electro-motive force of magnesium. Suitable ceramic nanoparticles are available from SkySpring Nanomaterials, Houston Tex.

The microstructures provided herein can include equiaxed Mg-rich solid solution-phase grains with second-phase precipitates and/or ceramic nanoparticles located within smooth and equiaxed alpha-phase-grain boundaries. In some cases, the equiaxed equiaxed Mg-rich solid solution-phase grains have an average grain size of 20 microns or less, 15 microns or less, 10 microns or less, 7.5 microns or less, 5 microns or less, 4 microns or less, 3 microns or less, 2 microns or less, or 1 microns or less. In some cases, the equiaxed Mg-rich solid solution-phase grains have an average grain size of between 0.1 microns and 10 microns, of between 0.5 microns and 5 microns, or between 1 micron and 4 microns. In some cases, at least 90% by volume of the secondary phase particles can be found along alpha phase grain boundaries. In some cases, the average secondary phase individual particle diameter or longest dimension is 1 microns or less, 500 nanometers or less, 300 nanometers or less, 200 nanometers or less, 100 nanometers or less, 75 nanometers or less, 50 nanometers or less, or 25 nanometers or less. In some cases, the average secondary phase individual particle diameter or longest dimension is between 0.1 nanometers and 1 micron, between 0.5 nanometer and 500 nanometers, between 5 nanometers and 300 nanometers, between 10 nanometers and 200 nanometers, between 20 nanometers and 100 nanometers, between 25 nanometers and 75 nanometers, or between 40 nanometers and 60 nanometers. The microstructure provided herein can have a reduced number of twin bands. In some cases, less than 15% of the alpha grains will have twin bands. In some cases, the number of alpha grains having twin bands can be less than 10%, less than 5%, or less than 1% when the stent is cut and crimped.

Microstructures provided herein can have enhanced ductility. The microstructures provided herein can overcome the basal plane alignment by randomizing grain orientations and result in isotropic mechanical properties. Finer grains also yield increased grain boundary areas, which can provide more grain boundary slip. Refinement of precipitate diameter may also allow additional grain boundary slip. Moreover, a homogenous dispersion of secondary-phase precipitates and/or ceramic nanoparticles along the grain boundaries can improve strength and corrosion resistance. In some cases, the precipitates and/or ceramic nanoparticles can be substantially centered on the grain boundary but be larger than the width of the grain boundary.

For example, a tubular body (e.g., stent tubing material) made from a bioerodible magnesium alloy formulation provided herein can be made by a process as described below. The bioerodible magnesium alloy can include, for example, 3.5 weight percent Y, 1.0 weight percent Nd, 2.0 weight percent Gd, 0.5 weight percent Dy, 8 weight percent Ho, 3.0 weight percent Tm, 3.0 weight percent Tb, 0.5 weight percent Zr, and a balance of Magnesium. The bioerodible magnesium alloy formulation provided herein can have an elastic modulus of between 39 and 200 GPa, a 0.2% Offset Yield Strength of between 150 and 600 MPa, an ultimate tensile strength of between 225 and 600 MPa, and/or a tensile reduction in area (RIA) of between 30% and 80%. In some cases, stent tubing material provided herein can have a tensile RIA of between 45% and 80%. In some cases, stent tubing material provided herein can maintain its initial elastic modulus, Yield Strength, ultimate tensile strength, and a tensile RIA within +/−10% after storage of the tubing for 180 days at a temperature of between 20° C. and 25° C. and a relative humidity of less than 30%.

Table III

Bioerodible magnesium alloys having a microstructure provided herein can be polished to have a smooth surface finish. In some cases, an endoprosthesis provided herein can have a surface including a bioerodible magnesium alloy having a surface roughness $R_a$ of less than 0.5 microns, less than 0.4 microns, less than 0.3 microns, less than 0.2 microns, less than 0.1 microns, or less than 0.05 microns. Bioerodible magnesium alloys having microstructure provided herein can have improved corrosion resistance, which can provide a slower bioerosion rate. A stent body of a bioerodible magnesium alloy having a microstructure provided herein can have an in-vitro corrosion penetration rate of less than 200 μm/year after a period of 28 days of continuous immersion in non-flowing, agitated Simulated Body Fluid (agitated at 60 rpm) at 37° C. where the Simulated Body Fluid ("SBF") is present in an amount of at least 10 times the initial volume of the stent material. The ingredients of SBF, which are added to water, are shown in Table III.

TABLE III

| SBF Ingredients | |
| --- | --- |
| Chemical | Mass/Volume |
| NaCl | 5.403 g |
| NaHCO$_3$ | 0.504 g |
| Na$_2$CO$_3$ | 0.426 g |
| KCl | 0.225 g |
| K$_2$HPO$_4$•3H$_2$O | 0.230 g |
| MgCl$_2$•6H$_2$O | 0.311 g |
| 0.2M NaOH | 100 mL |
| HEPES | 17.892 g |
| CaCl$_2$ | 0.293 g |
| Na$_2$SO$_4$ | 0.072 g |

Microstructures provided herein can be formed by using the following process steps: (a) mix elements to form a molten magnesium alloy (and optionally add ceramic nanoparticles); (b) cooling the molten magnesium alloy to form a ingot or billet; (c) solution treating a billet to solutionize any intermetallic precipitates formed during solidification of the alloy; (d) controlled cooling after solutionizing to form a distribution of fine discontinuous or continuous precipitates along grain boundaries; and (e) thermomechanical deformation of the material after or during cooling to refine the Mg-rich solid solution grain size and produce a substantially equiaxed grain morphology.

For example, an ingot or billet can be formed or machined into a solid or hollow rod, homogenized, subjected to a high-strain process to refine the microstructure, and then shaped or machined into stent tubing from which the stent is manufactured into final dimensions (e.g., the dimensions of a stent body). In some cases, a billet or ingot provided herein can be formed into an endoprosthesis that does not normally undergo expansion, for example vascular closing plugs or embolical material (e.g., microbeads used to close off unwanted vascular structures or cancerous tissue).

Figure 2:
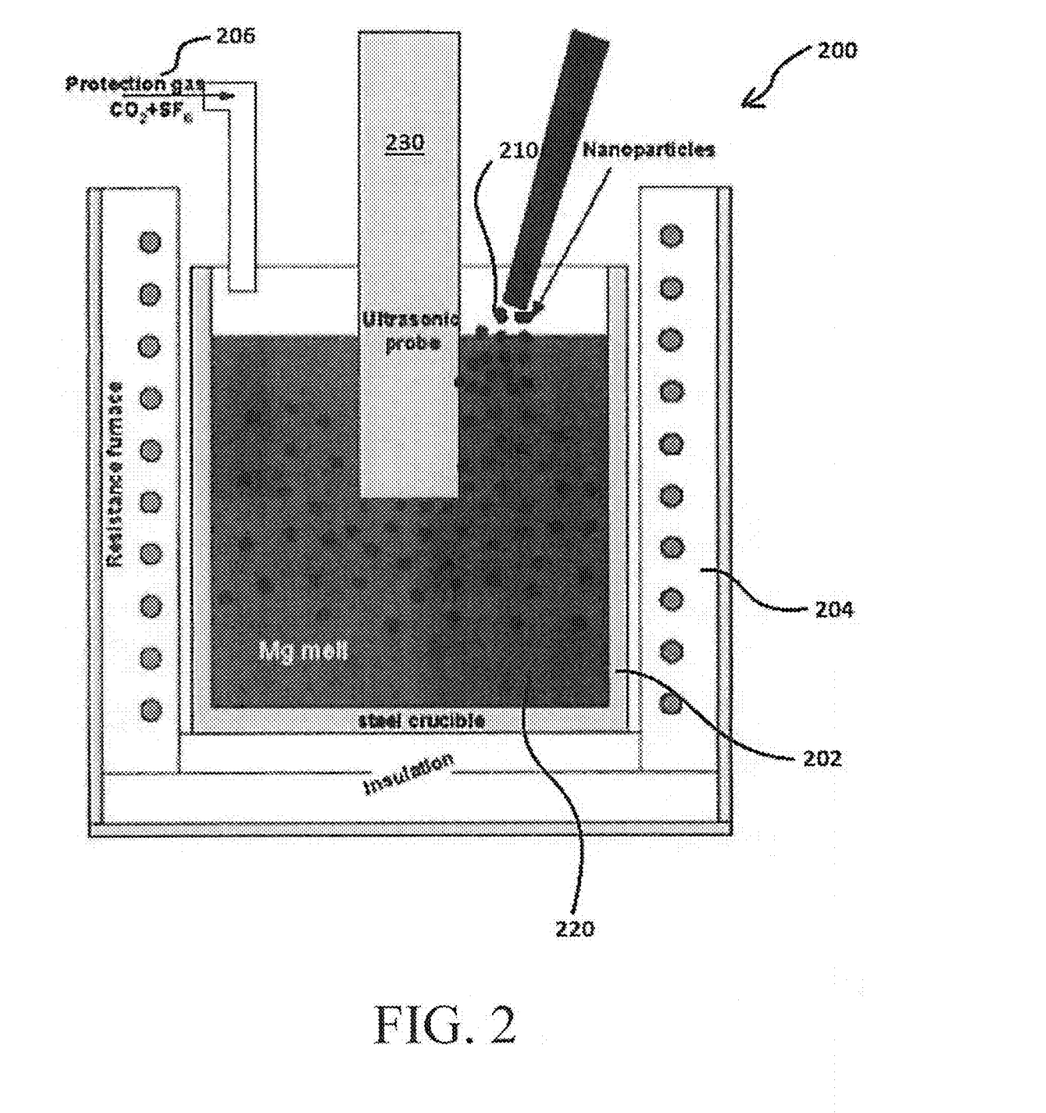
FIG. 2 depicts an exemplary arrangement for fabricating a magnesium-alloy ceramic-nanoparticle composite.

Ceramic nanoparticles can optionally be dispersed within a molten magnesium alloy using any suitable method. FIG. 2 depicts an exemplary arrangement 200 for introducing ceramic nanoparticles 210 into a molten magnesium alloy 220. Magnesium metal and one or more alloying constituents (e.g., aluminum) can be introduced to a steel crucible 202 within a resistance furnace 204. In some case, magnesium is alloyed with alloying elements prior to introduction to steel crucible 202 or resistance furnace 204. In some cases, magnesium is alloyed with alloying elements in steel crucible 202 before, after, or concurrently with an addition of ceramic nanoparticles. A protection gas 206 can be used to prevent unwanted reactions or exposure to oxygen. In some cases, energy can be used to prevent ceramic nanoparticles from agglomerating during the mixing process. For example, an ultrasonic probe 230 can be placed within steel crucible 202 to impart ultrasonic energy to the mixture. The mixture can then be cooled to form a billet or ingot.

Billets can be made using any suitable process. A billet can have a diameter of between 2 centimeters and 1 meter. In some cases, an ingot of a desired bioerodible magnesium alloy can be made by conventional melting and solidification in a mold (liquid casting), thixomolding (semi-solid processing) or powder metallurgy (solid-processing). The ingot can then be machined to the desired dimensions of the billet which will serve as the feedstock for subsequent processing and shaping. In some cases, a billet can be formed without additional machining process. To form an endoprosthesis (e.g., a stent body) out of a billet, the billet can be converted into a rod or hollow tube having a smaller diameter. In some cases, the ingot or billet is converted into a rod or hollow tube after the ingot or billet is homogenized. In some cases, the rod or hollow tube can have an outer diameter of between 1 centimeter and 6 centimeters. In the case of a stent, a hollow tube provided herein can then be further reduced in diameter and cut to form individual stent bodies, including fenestrations between stent struts. In some cases, the stent struts can have a width to thickness ratio of less than 1.2. In some cases, the thickness of the hollow tube and the stent struts can be between 80 microns and 160 microns.

An ingot or billet, in some cases, can be made by thixomolding the elements of the bioerodible magnesium alloy (and optionally ceramic nanoparticles). Thixomolding involves mixing solid constituents into a portion of the composition that is in a liquid phase and then cooling the mixture to reach a fully solid state. Thixomolding can reduce the number and size of brittle inter-metallic (IM) particles in the alloy. For example, thixomolding can use a machine similar to an injection mold. Room temperature magnesium alloy chips, chips of the other alloy constituents, and optionally ceramic nanoparticles can be fed into a heated barrel through a volumetric feeder. The heated barrel can be filled with an inert gas (e.g., argon) to prevent oxidation of the magnesium chips. A screw feeder located inside the barrel can feed the magnesium chips and other alloy constituents forward as they are heated into a semi-solid temperature range. For example, the mixture can be heated to a temperature of about 442° C. The screw rotation can provide a shearing force that can further reduce the size of IM particles. Once enough slurry has accumulated, the screw can move forward to inject the slurry into a steel die having the shape of an ingot or billet.

An ingot or billet, in some cases, can be made by combining the elements of the bioerodible magnesium alloy using powder metallurgy. Powder metallurgy involves the solid-state sintering of elemental or pre-alloyed powder particles and optionally ceramic nanoparticles. Using fine powders in a sintering process can avoid the formation of coarse IM particles. For example, fine powders of magnesium, other alloying constituents, and optionally ceramic nanoparticles can be blended into a homogenous mixture, pressed into a desired shape (e.g., the shape of the ingot or billet), and heated while compressed to bond the powders together. Sintering can be conducted in an inert atmosphere (e.g., argon) to avoid oxidation of the magnesium.

An ingot or billet including all of the desired elements of a bioerodible magnesium alloy and the optional ceramic nanoparticles can be homogenized to reduce elemental concentration gradients. The ingot or billet can be homogenized by heating the ingot or billet to an elevated temperature below the liquidus temperature of the bioerodible magnesium alloy and holding the ingot or billet at that temperature for period of time sufficient to allow elemental diffusion within the ingot or billet to reduce elemental concentration gradients within the ingot or billet.

Homogenizing the ingot or billet can solutionize intermetallic (IM) second-phase precipitate particles, because the homogenization temperature is in excess of the phase boundary (solvus temperature) between the high-temperature single, solid phase (alpha) and two-phase field boundary on the Mg—Al phase diagram. A follow-on solutioning treatment at the same or similar position within the phase diagram can be used in some cases to refine the precipitate structure. For example, a follow-on solutioning treatment can be used if the homogenization treatment cooling was not controlled sufficiently to tailor the second-phase precipitate size and location. In some cases, the ingot or billet is cooled rapidly after holding the ingot or billet at the elevated temperature in order to form relatively fine IM second-phase precipitates. For example, the ingot or billet can be cooled from the elevated hold temperature via force gas cooling or liquid quenching. The ingot or billet can be homogenized in an inert atmosphere (e.g., in an argon atmosphere) or open atmosphere so long as surface oxides are removed. In some cases, the ingot or billet provided herein can be homogenized at a temperature of between 400° C. and 450° C. In some cases, the ingot or billet is held at a temperature of between 400° C. and 450° C. for at least 2 hours, at least 3 hours, or at least 4 hours. In some cases, the hold time at an elevated temperature is between 4 hours and 24 hours. For example, a bioerodible magnesium alloy ingot having a diameter of about 15 centimeters can be heated to a temperature of 440° C. for 6 hours to homogenize the ingot, followed by quenching the ingot in a cooled argon gas stream.

An ingot or billet can be subjected to one or more high-strain processes to refine the microstructure into a microstructure provided herein. In some cases, the high-strain process(es) can include one or more equal-channel high-strain processes. Equal-channel high-strain processes include Equal-Channel Angular Extrusion ("ECAE") and Equal-Channel Angular Pressing ("ECAP"). ECAE is an extrusion process that produces significant deformation strain without reducing the cross sectional area of the piece. ECAE can be accomplished by extruding the alloy (e.g., a billet of the alloy) around a corner. For example, a billet of a bioerodible magnesium alloy provided herein can be forced through a channel having a 90 degree angle. The cross section of the channel can be equal on entry and exit. The complex deformation of the metal as it flows around the corner can produce very high strains. In some cases, an ingot can be machined into a billet having the exact dimensions of the channel of an ECAE die prior to an ECAE process. Because the cross section can remain the same, the billet can be extruded multiple times with each pass introducing additional strain. With each ECAE process, the orientation of the billet can be changed to introduce strain along different planes. In some cases, an ECAE die can include multiple bends. For example, FIG. 3 depict an example of an ECAE die.

Figure 3:
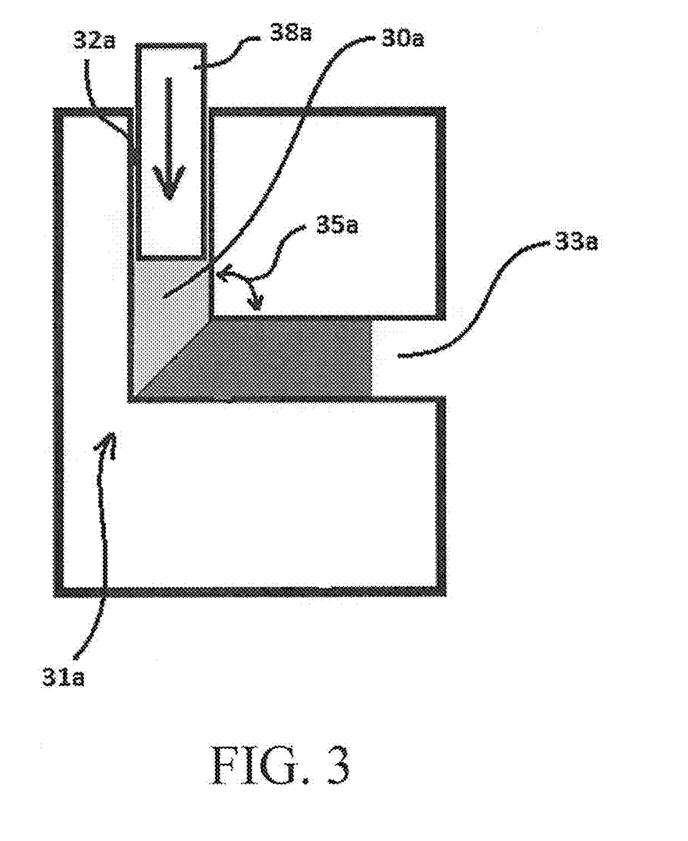
FIG. 3 depicts an exemplary Equal-Channel Angular Extrusion die.

The ingot or billet provided herein can be extruded through one or more ECEA dies (e.g., as depicted in FIG. 3) at temperatures lower than a homogenization temperature. Multiple equal-channel high-strain extrusions can be performed at subsequently lower temperatures. The equal-channel high-strain processes can yield a fine grain size with fine secondary-phase precipitates (i.e., IM particles) that are primarily located along the grain boundaries. The optional ceramic particles can also become located along the grain boundaries if included. In some cases, the dynamic recrystallization of the grain refinement caused by successive equal-channel high-strain extrusions at declining temperatures can introduce more strain into the material and result in finer grain sizes as compared to cold working and annealing steps. In some cases, an ingot or billet is subjected to at least two ECAE processes at two different sequentially-lower temperatures. In some cases, an ingot or billet is subjected to at least three ECAE processes at different sequentially-lower temperatures.

For example, a billet including a magnesium-aluminum alloy can be processed through two ECAE processes, with the first ECAE process occurring at a higher temperature than the second ECAE process. Each process can occur through a simple ECAE die have a single 90° corner, such as that depicted in FIG. 3. The first ECAE process can be conducted at a temperature of between 250° C. and 400° C. to allow good diffusion of rare earth elements to the grain boundaries. The first ECAE process can result in a microstructure having an average grain diameter of 15 microns or less. A second ECAE process can be done at a temperature of between 150° C. and 300° C. The second ECAE process can further refine the grain sizes and avoid coarsening.

In the ECAE process shown in FIG. 3, an ingot or prior-worked billet 30a is extruded through a channel 31a including two channel portions 32a, 33a of substantially identical cross-sectional areas having the respective center-lines thereof disposed at an angle 35a. As shown, angle 35a can be about 90°. In some cases, angle 35a can be between 45° and 170°, between 50° and 160°, between 60° and 135°, between 70° and 120°, between 80° and 100°, or between 85° and 95°. Billet 30a can have any appropriate cross section and machined to provide a snug fit into entry channel portion 32a. In some cases, billet 30a can have a circular cross sectional shape. A ram 38a can force billet 30a through channel 31a using an appropriate extrusion ram pressure. The strain imposed on billet 30a is a function of angle 35a.

Composites provided can, in some cases, be made by sintering powders of metal alloy and ceramic nanoparticles together. In some cases, powder metallurgy techniques can be used to form a composite provided herein.

The billet can be formed into a rod or hollow tube having a reduced outer diameter after one or more high-strain processes. Tube or rod drawing from the billet can occur in multiple steps, with optional intermediate and final annealing steps, to reduce the diameter. The drawing and annealing processes can be controlled to preserve the microstructure formed in the one or more high-strain processes. In some cases, the material is annealed at a temperature of less than 300° C. In some cases, the material is annealed at a temperature of between 150° C. and 300° C., between 150° C. and 250° C., or between 150° C. and 200° C. Annealing steps can be used to allow recovery with limited recrystallization and avoid grain growth or changes in precipitate volume fraction and morphology. Annealing steps can also maintain a homogenous dispersion of secondary-phase precipitates at the grain boundaries.

Individual stent bodies can then be cut, including cutting fenestrations between stent struts, using any suitable technique. For example, the fenestrations can be cut using a laser.

A coating can be applied over a bioerodible magnesium alloy or composite of an endoprosthesis provided herein. For example, a stent provided herein can include a stent body formed of a bioerodible magnesium alloy including a microstructure or composite provided herein and a coating overlying the surface of the stent body. A coating can slow or delay the initial degradation of the bioerodible magnesium alloy or composite upon placement within a physiological environment by serving as a temporary barrier between the magnesium alloy and the environment. For example, delaying the bioerosion processes can allow the body passageway to heal and a stent to become endothelialized (surrounded by tissues cells of the lumen wall) before the strength of the stent is reduced to a point where the stent fails under the loads associated with residing within a body lumen (e.g., within a blood vessel). When an endothelialized stent fragments, the segments of the stent can be contained by the lumen wall tissue and are thus less likely to be released into the blood stream. Endothelialization can also block the oxygen-rich turbulent flow of the blood stream from contacting the endoprosthesis, thus further reducing the erosion rate of the endoprosthesis. In some case, a stent provided herein can include a coating that includes titanium oxide, aluminum oxide, or a combination thereof. Examples of suitable coatings can be found in U.S. Patent Application Publication No. 2012/0059455, which is hereby incorporate by reference in its entirety, particularly the sections describing coatings formed by atomic layer deposition.

In some cases, an endoprosthesis provided herein can include a sprayed layer of magnesium fluoride nanoparticles. Magnesium fluoride suspensions can be applied to an endoprosthesis provided herein using a suspension plasma spray (SPS) process, which can deliver nearly monodisperse nanoparticles in a gram scale yield to provide a protective magnesium fluoride layer. The SPS process can use a Sulzer Metco Triplex II torch attached on an ABB industrial robot.

The stent can optionally include a therapeutic agent. In some cases, the coating can include a therapeutic agent. In some cases, the coating can include a polymer (e.g., a bioerodible polymer). For example, a drug-eluting polymeric coating can be applied to the stent body provided herein. In some cases, a stent provided herein can be essentially polymer-free (allowing for the presence of any small amounts of polymeric materials that may have been introduced incidentally during the manufacturing process such that someone of ordinary skill in the art would nevertheless consider the coating to be free of any polymeric material). The therapeutic agent may be any pharmaceutically acceptable agent (such as a drug), a biomolecule, a small molecule, or cells. Exemplary drugs include anti-proliferative agents such as paclitaxel, sirolimus (rapamycin), tacrolimus, everolimus, biolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, lipids, and compounds have a molecular weight of less than 100 kD. Exemplary cells include stem cells, progenitor cells, endothelial cells, adult cardiomyocytes, and smooth muscle cells.

A stent provided herein can include one or more imaging markers. Imaging markers can assist a physician with the placement of the stent. Imaging markers can be radiopaque marks to permit X-ray visualization of the stent.

Stent 20 can be configured for vascular, e.g., coronary and peripheral vasculature or non-vascular lumens. For example, it can be configured for use in the esophagus or the prostate. Other lumens include biliary lumens, hepatic lumens, pancreatic lumens, and urethral lumens.

Stent 20 can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some cases, a peripheral stent can have an expanded diameter of from about 4 mm to about 24 mm. In certain embodiments, a gastrointestinal and/or urology stent can have an expanded diameter of from about 6 mm to about 30 mm. In some cases, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., see U.S. Pat. No. 6,290,721).

Non-limiting examples of additional endoprostheses that can include a bioerodible magnesium alloy including a microstructure provided herein include stent grafts, heart valves, and artificial hearts. Such endoprostheses are implanted or otherwise used in body structures, cavities, or lumens such as the vasculature, gastrointestinal tract, lymphatic system, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like. In some cases, an endoprosthesis can include a biodegradable scaffold for the lymphatic system.

EXAMPLE

A sample AZNd alloy having the elements listed in Table II was produced as discussed herein and extruded at 400° C. Samples of AZNd alloy were tested for expansion failures and compared to a control alloy L1c. As shown in Table IV below, the AZNd alloy demonstrated suitable mechanical properties for a nominal expansion of 3.0 mm.

TABLE IV

Mg Stent Design and Material Development and Testing

| Test Results | Material | | | | | |
|---|---|---|---|---|---|---|
| | L1c | L1c | L1c | AZNd | AZNd | AZNd |
| 3.0 mm ID Deploy Fractures | 5/9 | 0/5 | 0/9 | 0/6 | 0/3 | 0/3 |
| Overexpansion Fractures | No Test | 5/5 | 5/5 | 3/3 | 3/3 | 2/2 |
| Ave. Overexpansion OD (mm) | No Test | 3.97 | 4.36 | 4.22 | 3.63 | 3.69 |

Figure 4A:
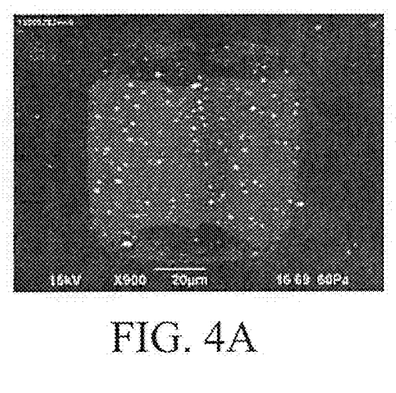
FIG. 4A depicts a post-test SEM WE43 element stent as received.
Figure 4B:
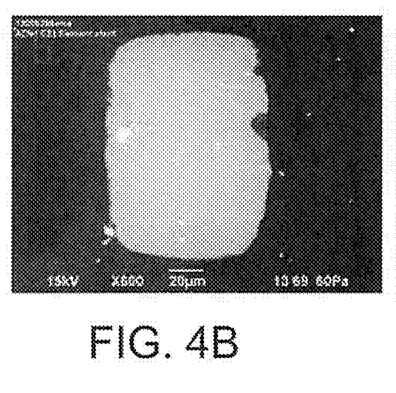
FIG. 4B depicts a post-test SEM AZNd element sent as received.
Figure 4C:
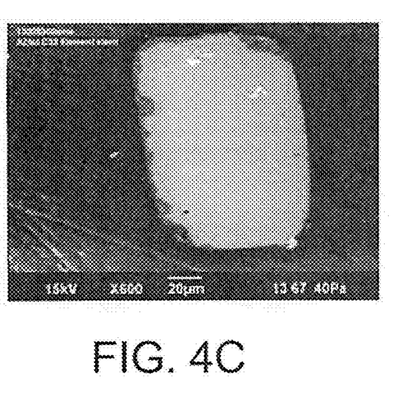
FIG. 4C depicts a post-test SEM AZNd element stent nominally expanded to 3.0 mm.
Figure 4D:
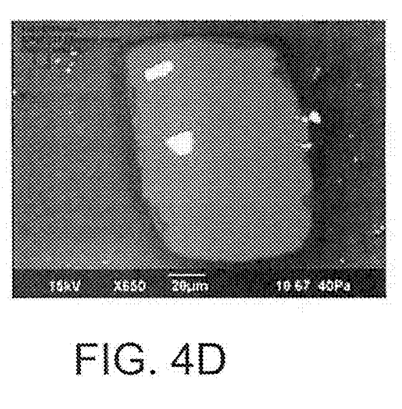
FIG. 4D depicts a post-test SEM AZNd element sent overexpanded beyond 3.0 mm.

FIGS. 4A-4D show SBF Immersion results for stents. The stents were immersed in SBF for 54 hours. FIG. 4A depicts a post-test SEM WE43 element stent as received. FIG. 4B depicts a post-test SEM AZNd element sent as received. FIG. 4C depicts a post-test SEM AZNd element stent nominally expanded to 3.0 mm. FIG. 4D depicts a post-test SEM AZNd element sent overexpanded beyond 3.0 mm. As shown, the AZNd element stents had a more even and slower erosion rate as compared to the WE43 element control. The AZNd element stent had an alpha grain size of about 11 microns.

Figure 5:
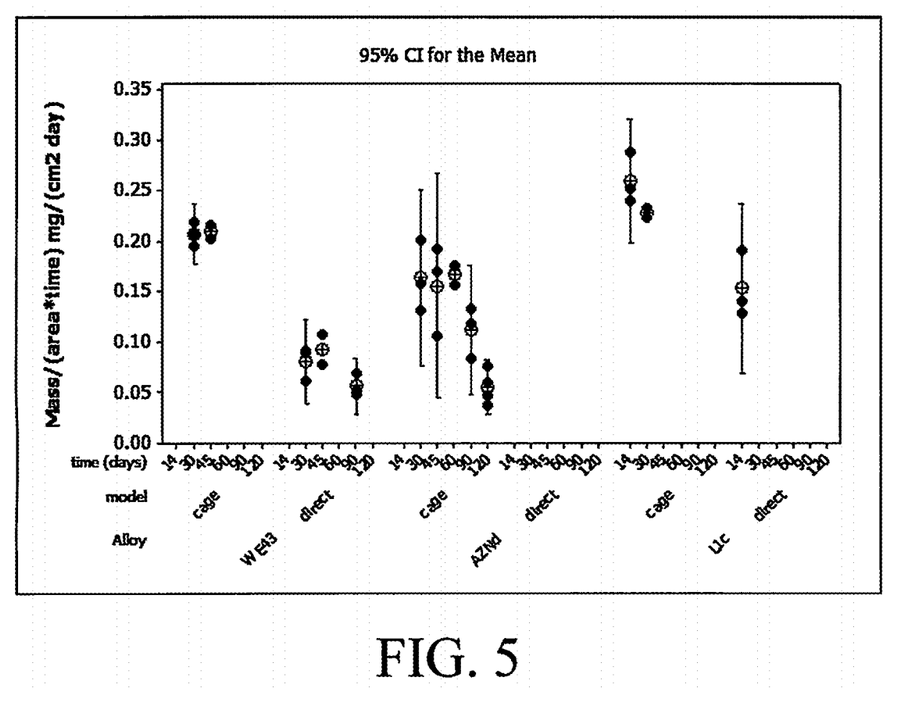
FIG. 5 depicts the mass loss per area over time for a WE43 element stent, a AZNd element stent, and a L1c element stent in a rat subcutaneous model.

FIG. 5 depicts the mass loss per area over time for a WE43 sheet, a AZNd hypotube section, and a L1c hypotube section in a rat subcutaneous model. The AZNd alloy was produced as discussed herein and extruded at 400° C. The AZNd hypotube section was placed in a rat in a PMMA cage for 120 days. The WE43 sheet was placed in a PMMA cage for 45 days and direct subcutaneous for 90 days. The L1c was placed in a PMMA cage for 30 days and direct subcutaneous for 15 days. The data in FIG. 5 shows the change in mass for the sample over time (after washing away salts). As shown in FIG. 5, during the initial degradation during days 0-45, the AZNd element stent had a slower degradation than the WE43 element stent by about 1.5 times followed by further slowing down.

All publications, patent applications, patents, and other references mentioned herein are incorporated by reference herein in their entirety.

Still further embodiments are within the scope of the following claims.

What is claimed is:

1. A method of processing a bioerodible magnesium alloy for a stent comprising:
   forming an ingot or billet comprising a molten magnesium alloy comprising from 50 weight percent to 92 weight percent magnesium, from 5.5 weight percent in sum to 50 weight percent in sum of one or more elements selected from the group consisting of Ho, Er, Lu, Tb and Tm, and from 2.0 weight percent in sum to 50 weight percent in sum of one or more elements selected from the group consisting of Y, Nd and Gd;
   cooling the molten magnesium alloy to form an ingot or billet; and
   performing at least one process, comprising Equal-Channel Angular Extrusion (ECAE) or Equal-Channel Angular Pressing (ECAP), on the ingot or billet to form a microstructure comprising equiaxed Mg-rich solid solution-phase grains having an average grain diameter of less than or equal to 15 microns and continuous or discontinuous second-phase precipitates or ceramic nanoparticles in grain boundaries between the equiaxed Mg-rich solid solution-phase grains, the second-phase precipitates or ceramic nanoparticles having an average longest dimension of 2.0 micron or less; and
   performing an intermediate annealing of the ingot or billet after performing the at least one ECAE or ECAP process on the ingot or billet at a temperature of from 150° C. and 250° C.

2. The method of claim 1, further comprising holding the ingot or billet at a temperature of between the solvus and liquidus boundaries of the phase diagram for at least 2 hours to homogenize the ingot or billet before preforming the at least one ECAE or ECAP process on the ingot or billet.

3. The method of claim 1, wherein the at least one ECAE or ECAP process is preformed at a temperature of less than 400° C., wherein the ingot or billet is processed through at least two ECAE or ECAP processes at different temperatures, wherein a first ECAE or ECAP process occurring at a first time is performed at a higher temperature than a second ECAE or ECAP process occurring at a second time after the first time, wherein the first ECAE or ECAP process is performed at a temperature of between 250° C. and 400° C. and the second ECAE or ECAP process is performed at a temperature of between 150° C. and 300° C.

4. The method of claim 3, further comprising performing a final annealing of the ingot or billet at a temperature of from 150° C. and 250° C. after performing the second ECAE or ECAP process on the ingot or billet.

5. The method of claim 4, wherein the ingot or billet processed in the first ECAE or ECAP process or the second ECAE or ECAP process is extruded through an equal-channel angular extrusion die having two-channels comprising identical cross-sectional areas having respective centerlines thereof disposed at an angle of from 45° and 170°.

* * * * *